United States Patent [19]

Schlecker et al.

[11] Patent Number: 4,463,007
[45] Date of Patent: Jul. 31, 1984

[54] TRIAZOLOQUINAZOLINONES, AND COMPOSITIONS AND METHODS FOR TREATING ALLERGIC DISORDERS WITH THEM

[75] Inventors: Rainer Schlecker, Bissersheim; Ludwig Friedrich, Bruehl; Dieter Lenke, Ludwigshafen, all of Fed. Rep. of Germany

[73] Assignee: BASF Aktiengesellschaft, Fed. Rep. of Germany

[21] Appl. No.: 441,805

[22] Filed: Nov. 15, 1982

[30] Foreign Application Priority Data

Nov. 25, 1981 [DE] Fed. Rep. of Germany ....... 3146599

[51] Int. Cl.³ ................. A61K 31/505; C07D 487/04
[52] U.S. Cl. .................................... 424/251; 544/247; 544/251
[58] Field of Search ................ 544/25.1, 247; 424/251

[56] References Cited

U.S. PATENT DOCUMENTS 3,850,932 11/1974 Kathawala et al. ................ 544/251
4,053,600 10/1977 Hardtmann et al. ............... 424/250
4,128,644 12/1978 Vogt .................................... 424/251
4,164,578 8/1979 Vogt .................................... 424/251

OTHER PUBLICATIONS

Reimlinger, et al., Chem. Ber., 108, pp. 3799–3806 (1975).
Brown, et al., Aust. J. Chem., 32, pp. 1585–1593 (1979).

Primary Examiner—Donald G. Daus
Assistant Examiner—Diana G. Rivers
Attorney, Agent, or Firm—Keil & Weinkauf

[57] ABSTRACT 1,2,4-Triazolo[1,5-c]-quinazolinones of the general formula I

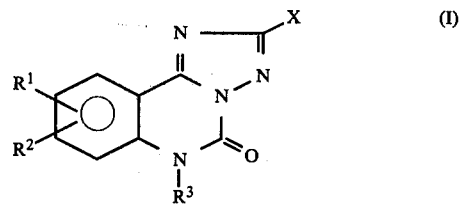

and their pharmaceutically tolerated salts, processes for their preparation and pharmaceutical formulations which contain these compounds and are useful drugs in the treatment of allergic disorders.

11 Claims, No Drawings

TRIAZOLOQUINAZOLINONES, AND COMPOSITIONS AND METHODS FOR TREATING ALLERGIC DISORDERS WITH THEM

The present invention relates to 1,2,4-triazolo-[1,5-c]quinazolinones of the general formula I and their pharmaceutically tolerated salts, processes for their preparation and pharmaceutical formulations which contain these compounds and are useful drugs in the treatment of allergic disorders.

U.S. Pat. No. 4,164,578 discloses pyrazoloquinazolines which may be used as antiallergic agents, but the actions of these compounds are not always satisfactory.

We have found that compounds of the formula I

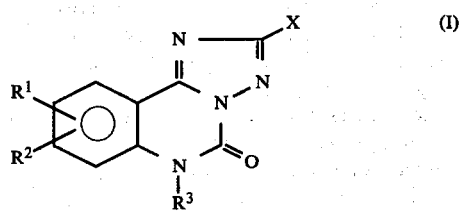

where X is carboxyl which may be in the form of a salt with a physiologically tolerated amine or metal cation, or is

where $R^4$ is alkyl of 1 to 8 carbon atoms, cycloalkyl of 3 to 8 ring carbon atoms, benzyl, or $-(CH_2)_n-O-R^5$ or

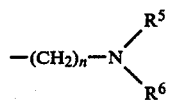

where n is an integer from 2 to 4 and $R^5$ and $R^6$ are each alkyl of 1 to 3 carbon atoms, or X is hydroxymethyl, nitrile, tetrazolyl, carbonylaminotetrazolyl or carbamyl, and $R^1$ and $R^2$ are identical or different and are each hydrogen, fluorine, chlorine, bromine, alkyl of 1 to 5 carbon atoms, trifluoromethyl, nitro, amino, an alkyl, monoalkylamino or dialkylamino group where alkyl is of 1 to 5 carbon atoms, alkoxy where alkyl is of 1 to 6 carbon atoms, or an alkylthio, alkylsulfenyl, alkylsulfonyl or dialkylaminosulfonyl radical where alkyl is of 1 to 6 carbon atoms, or $R^1$ and $R^2$ together form an alkylenedioxy group $-O-(CH_2)_n-O-$ where n is 1 or 2, or an alkylene group $-(CH_2)_n-$ where n is 3, 4 or 5, and $R^3$ is hydrogen, alkyl which is of 1 to 7 carbon atoms and may or may not be interrupted by 1 or 2 oxygen atoms, alkenyl of 2 to 7 carbon atoms or aralkyl of 7 to 10 carbon atoms, and their physiologically tolerated addition salts with acids, possess useful pharmacological properties, in particular as antiallergic agents.

From amongst the meanings given above, a preferred meaning of X is

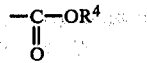

where $R^4$ is alkyl of 1 to 8, in particular 1 to 4, carbon atoms, preferred meanings of $R^1$ and $R^2$, which may be identical or different, are hydrogen, fluorine, chlorine, bromine and alkyl of 1 to 5, in particular 1 to 3, carbon atoms, and a preferred meaning of $R^3$ is alkyl of 1 to 7, in particular 1 to 4, carbon atoms.

Specific examples of alkyl radicals $R^1$ and $R^2$ are methyl, ethyl, propyl, isopropyl, butyl, isobutyl, pentyl and isoamyl. Specific examples of alkylamino radicals $R^1$ and $R^2$ are methylamino, ethylamino, propylamino, isopropylamino, cyclopropylamino, sec.-butylamino, butylamino, amylamino, isoamylamino and hexylamino. Specific examples of alkoxy radicals $R^1$ and $R^2$ are methoxy, ethoxy, propoxy, isopropoxy, butoxy, tert.-butoxy, i-butoxy, isoamyloxy and hexyloxy. Specific examples of alkylthio radicals $R^1$ and $R^2$ are methylthio, ethylthio, propylthio, isopropylthio, butylthio, sec.-butylthio, amylthio, neopentylthio and hexylthio. Specific examples of alkylsulfenyl radicals $R^1$ and $R^2$ are methylsulfenyl, ethylsulfenyl, propylsulfenyl and butylsulfenyl. Specific examples of alkylsulfonyl radicals $R^1$ and $R^2$ are methylsulfonyl, ethylsulfonyl, propylsulfonyl, isopropylsulfonyl, butylsulfonyl, iso-butylsulfonyl, pentylsulfonyl, isopentylsulfonyl and hexylsulfonyl. Specific examples of alkylene radicals formed from $R^1$ and $R^2$ are propylene, butylene, 1-methylbutylene, 2-methylbutylene and pentylene. Specific examples of alkyl radicals $R^3$ which may or may not be interrupted by 1 or 2 oxygen atoms are methyl, ethyl, propyl, methoxymethyl, methoxyethyl, isopropyl, butyl, isobutyl, ethoxyethyl, pentyl, isoamyl, hexyl, heptyl and methoxyethoxymethyl. Specific examples of alkenyl radicals $R^3$ are allyl, buten-1-yl, buten-2-yl, 2-methylpropenyl, penten-1-yl, penten-2-yl, penten-3-yl, hexen-2-yl, hexen-3-yl, hepten-2-yl and hepten-3-yl. Specific examples of aralkyl radicals $R^3$ are benzyl, phenylethyl, 2-phenylethyl, phenylpropyl and phenylbutyl.

The compounds of the general formula I are prepared by a process wherein a hydrazinoquinazoline of the general formula II

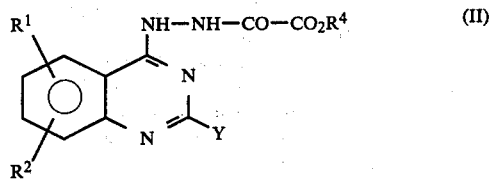

where $R^1$, $R^2$ and $R^4$ have the meanings given for formula I and Y is hydroxyl, bromine or chlorine, is subjected to an intramolecular condensation reaction, preferably in the presence of a dehydrating agent, in particular phosphorus oxychloride, a polyphosphoric acid or acetic acid, in the presence or absence of an inert solvent, eg. toluene, chlorobenzene, or xylene, or of excess acetic acid, at from 50° to 150° C., preferably under reflux, and thereafter the resulting ester of formula I is, if required, alkylated in a conventional manner at the N atom, the ester group is, if required, hydrolysed, and the acid obtained is, if necessary, converted into a salt with a physiologically tolerated amine or metal cation, or the initially obtained ester or the carboxylic acid is reacted further and the compound obtained converted, if required, into a pharmaceutically tolerated addition salt with an acid.

The preparation may be illustrated by the following example: the reaction according to the invention gives, as the primary cyclisation product, a 1,2,4-triazolo[4,3-c]quinazolinone of the general formula Ia

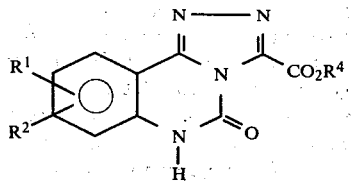

where $R^1$, $R^2$ and $R^4$ have the meanings given for formula II, and this product undergoes isomerization in an intramolecular Dimroth rearrangement, as described in, for example, Aust. J. Chem., 32 (1979) 1585–93, to give a compound of the general formula I. The structure of the novel compounds has been determined by X-ray analysis. Under the reaction conditions, the substituent Y is converted into a keto group.

The N atom in the 6-position is alkylated by reaction with an alkylating agent of the formula $R^3Z$ where Z is a nucleofugic leaving group, in particular chlorine, bromine, iodine or a sulfonic acid radical and $R^3$ has the meanings given in formula I, in the presence of an acid acceptor, advantageously at from 0° to 120° C., in an inert solvent, such as a lower alcohol of 1 to 4 carbon atoms, a dialkyl ether, a benzene hydrocarbon, eg. benzene or toluene, a lower ketone, eg. acetone, a dialkylformamide, eg. dimethylformamide, or dimethylsulfoxide. Particularly suitable acid acceptors are alkali metal and alkaline earth metal hydroxides, alkali metal and alkaline earth metal carbonates, alkali metal and alkaline earth metal alcoholates and alkali metal and alkaline earth metal hydrides. The stoichiometric amount or a slight excess of the acid acceptor is employed. In this reaction, dimethylformamide is the preferred solvent and sodium hydride the preferred base.

The resulting esters of the formula I can be transesterified in a conventional manner, in accordance with the meanings of the radical $R^4$.

Compounds of the general formula I where X and $R^3$ have the above meanings and $R^1$ and/or $R^2$ are each chlorine, nitro or sulfonylamido, may also be prepared by electrophilic aromatic substitution of a compound of the general formula I, where $R^1$ and $R^2$ are each hydrogen, by a conventional method, as described in, for example, Houben-Weyl, vol. X/1, pages 471 et seq, vol. IX, pages 572 et seq, and vol. V/3, page 873. Thus, it is possible to carry out nitration at room temperature using a mixture of sulfuric acid and nitric acid, sulfonation, for example, at from room temperature to 150° C. with chlorosulfonic acid, and chlorination at from 20° to 100° C. with sulfuryl chloride, ie. particular radicals $R^1$ and/or $R^2$ may be introduced subsequently.

Compounds of the general formula I where X is carboxyl are prepared by hydrolysing the corresponding esters, preferably under alkaline conditions, for example in the presence of an alkali metal hydroxide or sodium carbonate, in a solvent, such as water, a lower alcohol or tetrahydrofuran, or mixtures of these. The organic acid thus obtained may, if required, be converted into a physiologically tolerated amine salt or metal salt. For the purposes of the invention, these are, in particular, salts of alkali metals, eg. sodium and potassium, of alkaline earth metals, eg. calcium, and of other metals, eg. aluminum, and salts of organic bases, eg. morpholine, piperidine, monoethanolamine, diethanolamine or triethanolamine and tris-(hydroxymethyl)-aminomethane, which in general are known to the skilled worker.

The novel compounds obtained may, if required, be converted into addition salts with a physiologically tolerated acid. Examples of conventional physiologically tolerated inorganic acids which may be used are hydrochloric acid, hydrobromic acid, phosphoric acid and sulfuric acid, and examples of suitable organic acids are oxalic acids, maleic acid, fumaric acid, lactic acid, tartaric acid, malic acid, citric acid, salicylic acid, adipic acid and benzoic acid, and further examples may be found in Fortschritte der Arzneimittelforschung, 10 (1966), 224–225, Birkhäuser Verlag, Basel and Stuttgart.

Carboxylic acids of the general formula I may furthermore be prepared by hydrogenolysis of the corresponding benzyl esters by a conventional method, as described in, for example, Houben-Weyl, vol. IV/1c, pages 381 et seq. The reaction is carried out in the presence of a catalyst, such as platinum, palladium or nickel, advantageously on a carrier, in particular charcoal, in a solvent, such as a lower alcohol, in particular methanol, acetic acid or a dialkylformamide, in particular dimethylformamide, at from 0° C. to the boiling point of the solvent, preferably under only slightly superatmospheric pressure.

Amides of the general formula I where X is carbamyl, are obtained by reacting the ester with ammonia in the presence of a solvent, eg. water, of a lower alcohol, of an aqueous-alcoholic mixture or a dialkylformamide, at from 0° C. to the reflux temperature of the system.

The nitriles of the compounds of the general formula I where X is a nitrile group are obtained by treating the amide with a dehydrating agent, eg. phosphorus pentoxide, phosphorus oxychloride or thionyl chloride. The reaction is carried out in general under reflux, using an excess of the dehydrating agent. The reaction may be carried out in the presence or absence of an inert solvent, eg. benzene or ethylene chloride.

Compounds of the general formula I where X is tetrazolyl are synthesized by conventional methods, as described in, for example, Synth. 1973, 80, by reacting the amide with hydrazoic acid or with one of its salts, for example an alkali metal or alkaline earth metal azide, in the presence or absence of a Lewis acid, eg. aluminum chloride or tin chloride, or of ammonium chloride. Sodium azide and ammonium chloride constitute a preferred combination. In general, the reaction is carried out in the presence of an inert solvent, eg. benzene, tetrahydrofuran or dimethylformamide, at from room temperature to 150° C. The tetrazolyl compounds are strongly acidic, and may be converted in a conventional manner into salts with a physiologically tolerated amine or metal cation.

Reduction of a carboxylic acid, advantageously of an ester of a compound of the general formula I, by a conventional method, for example with the aid of a complex metal hydride, eg. lithium borohydride, in the presence of an ether, eg. tetrahydrofuran, as the solvent gives a hydroxymethyl compound of the general formula I where X is $CH_2OH$. The reduction is advantageously carried at the boiling point of the reaction mixture.

Compounds of the general formula I where X is carbonylaminotetrazolyl ($CO-NH-CHN_4$) can be obtained by a conventional method, by condensing the parent carboxylic acid with 5-aminotetrazole of the formula III

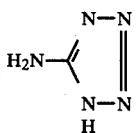 (III)

The reaction is carried out as a rule in an inert solvent, eg. methylene chloride, dioxane, tetrahydrofuran or dimethylformamide, preferably in the presence of a condensing agent conventionally employed in peptide chemistry, eg. N,N'-carbonyldiimidazole or N,N'-dicyclohexylcarbodiimide, at from 20° to 120° C.

The starting compounds of the general formula II are prepared in a conventional manner by condensing a hydrazinoquinazoline of the general formula IV

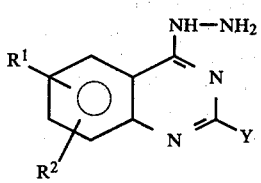 (IV)

where $R^1$ and $R^2$ have the meanings given for formula I and Y has the above meanings, with an oxalic acid ester halide, in particular ethyloxalyl chloride, or with an oxalic acid diester, preferably diethyl oxalate, the oxalic acid ester group being based on the alcohol $R^4OH$ where $R^4$ has the meaning given for formula II. When an oxalic acid ester halide, preferably a chloride, is employed, the reaction is advantageously carried out at from −30° to 70° C., preferably at room temperature, in an inert solvent, eg. dimethylformamide, dioxane, tetrahydrofuran or methylene chloride. The reaction is preferably carried out in the presence of a tertiary organic base, eg. triethylamine or pyridine.

The reaction of IV with an oxalic acid diester can be carried out in the presence or absence of a solvent, eg. toluene, chlorobenzene or diphenyl ether, at from about 20° C. to the reflux temperature of the mixture. The oxamate of the formula I can be transesterified with an alcohol by a conventional method, as described in, for example, Houben-Weyl, vol. 8, pages 526–528, to give an ester having a different radical $R^4$.

A further process for the preparation of starting compounds of the formula II comprises reacting an oxalylhydrazine of the general formula V $$H_2N-NH-CO-CO_2R^4$$ (V)

where $R^4$ has the above meanings, with a quinazoline of the general formula VI

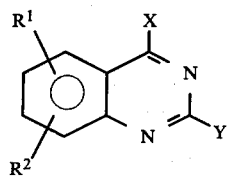 (VI)

where $R^1$, $R^2$ and Y have the above meanings and X may be a nucleofugic leaving group, preferably halogen, for example chlorine. The reaction is carried out at from 0° to 50° C. in an inert solvent, eg. ethanol, methylene chloride, toluene, tetrahydrofuran or dimethylformamide, preferably using an excess of V.

Advantageously, the compounds of the general formula IV are prepared by condensing a compound of the general formula VI with hydrazine. The process is carried out in a conventional manner, in general at from −20° to 50° C., in an inert solvent, eg. dioxane, tetrahydrofuran, methylene chloride or dimethylformamide.

The compounds of the general formula V are known, and may be prepared from a dialkyl oxalate and hydrazine, as described in, for example, Ber. dtsch. chem. Ges., 44 (1911) 776 et seq.

The compounds of the general formula VI where X and Y are each chlorine or bromine can be prepared by conventional methods described in, for example, J. Chem. Soc. 1948, 1759, by reacting the corresponding quinazoline-2,4-dione with phosphorus carboxychloride or phosphorus bromide, under reflux. Syntheses of the quinazoline-2,4-diones, which are likewise known, from an alkali metal isocyanate and anthranilic acid or an anthranilate, or from urea and an anthranilic acid derivative, are summarized in a review in W. L. F. Amarego, Quinazolines, pages 116–218, Wiley, 1967, New York.

Another process for the preparation of compounds of the general formula I comprises reacting a 3-(o-aminophenyl)-triazole of the formula VII

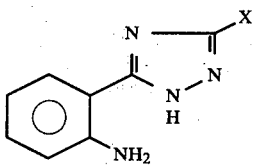 (VII)

with a carbonic acid derivative, eg. phosgene, a chloroformate or N,N'-carbonyldiimidazole. The reaction is preferably carried out in the presence of an inert organic solvent, eg. methylene chloride, benzene, ether or tetrahydrofuran, at from 0° C. to the boiling point of the solvent.

This cyclization may furthermore be carried out by reaction with urea at from 150° to 200° C., or with an alkali metal isocyanate in acetic acid.

The compounds of the formula VII can be prepared by a conventional method, by reducing the corresponding nitro derivatives. 3-(o-nitrophenyl)-triazoles are synthesized by conventional methods of triazole chemistry which are described in, for example, Heterocyclic Compounds, Vol. 7, pages 425 et seq., Wiley, 1961.

Specific examples of novel compounds are: 9-ethoxy-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl, and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9-propoxy-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9-hydroxy-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9-methoxy-1,2,4-triazolo[1,5-c]quinazoline-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9-propylsulfonyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4 methylpentyl, benzyl, n-heptyl, methoxyethyl, ethoxyethyl, 2-(dimethylamino)-ethyl and 3-(dimethylamino)-propyl esters of each of these; 9-ethylsulfinyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9-dimethylamino-1,2,4-triazolo[1,5-c]quinazoline-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9-ethylsulfonyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)propyl esters of each of these; 9-amino-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)propyl esters of each of these; 9-acetylamino-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 8-bromo-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 7-bromo-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 4-methylpentyl, benzyl, n-heptyl, methoxyethyl, ethoxyethyl, 2-(dimethylamino)-ethyl and 3-(dimethylamino)-propyl esters of each of these; 10-bromo-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9-bromo-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 8-chloro-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 7-chloro-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9-pentyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 10-chloro-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9,10-diethyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 8,9-diethyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9-propyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9-butyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 8,9-tetramethylene-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 8,9-trimethylene-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 7-ethyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9,10-dimethyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9-ethyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 8-ethyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 7-methyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 10-ethyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 10-methyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 8-methyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9-methyl-1,2,4-triazolo[1,5-c]quinazolin-5-one-2-carboxylic acid, its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-methoxyethoxymethyl derivatives, and the methyl, ethyl, propyl, isopropyl, cyclopropyl, allyl, n-butyl, tert.-butyl, sec.-butyl, n-pentyl, 2-methylbutyl, 3-methylbutyl, 2-methylpentyl, 3-methylpentyl, 4-methylpentyl, benzyl, n-heptyl, methoxyethyl, ethoxyethyl, 2-(dimethylamino)-ethyl and 3-(dimethylamino)-propyl esters of each of these; 9-dimethylamino-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-methylsulfonyl-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-ethylsulfonyl-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-ethylsulfonyl-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 1,2,4-triazolo[1,5-c]quinazolin-5-one-2-[N-(tetrazol-5-yl)-carboxamide] and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 2-hydroxymethyl-10-methyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 10-methyl-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 10-methyl-1,2,4-triazolo[1,5-c]quinazolin-5-one-2-[N-(tetrazol-5-yl)-carboxamide] and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 2-hydroxymethyl-9-methyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-methyl-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-methyl-1,2,4-triazolo[1,5-c]quinazolin-5-one-2-[N-tetrazol-5-yl)-carboxamide] and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 8-methyl-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 8-methyl-1,2,4-triazolo[1,5-c]quinazolin-5-one-2-[N-(tetrazol-5-yl)-carboxamide] and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 2-hydroxymethyl-7-methyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 7-methyl-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 7-methyl-1,2,4-triazolo[1,5-c]quinazolin-5-one-2[N-(tetrazol-5-yl)-carboxamide] and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 10-ethyl-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 1-ethyl-2-(tetrazol-5-yl)-1,2,4-triazolo[1,5-c]quinazolin-5-one- and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 10-ethyl-1,2,4-triazolo[1,5-c]quinazolin-5-one-2-[N-(tetrazol-5-yl)-carboxamide]

and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-ethyl-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-ethyl-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl 6-heptyl 6-methoxyethyl, 6-methoxyethoxymethyl and 6-ethoxyethoxymethyl derivatives; 9-ethyl-1,2,4-triazolo[1,5-c]quinazolin-5-one-2-[N-tetrazol-5-yl)-carboxamide] and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 8-ethyl-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 8-ethyl-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 8-ethyl-1,2,4-triazolo[1,5-c]quinazolin-5-one-2-[N-tetrazol-5-yl)-carboxamide] and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 7-ethyl-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 7-ethyl-2-(tetrazol-5-yl)-1,2,4-triazolo[1,5-c]quinazolin-5-one- and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 7-ethyl-1,2,4-triazolo[1,5-c]quinazolin-5-one-2-[N-(tetrazol-5-yl)-carboxamide] and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9,10-dimethyl-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9,10-dimethyl-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 2-hydroxymethyl-8,9-tetramethylene-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 8,9-tetramethylene-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 8,9-tetramethylene-1,2,4-triazolo[1,5-c]quinazolin-5-one-2-[N-(tetrazol-5-yl)-carboxamide] and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 2-hydroxymethyl-8,9-trimethylene-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 2-(tetrazol-5-yl)-8,9-trimethylene-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 2-hydroxymethyl-9-propyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-propyl-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-propyl-1,2,4-triazolo[1,5-c]quinazolin-5-one-2-[N-tetrazol-5-yl)-carboxamide] and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 2-hydroxymethyl-9-pentyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-pentyl-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9,10-diethyl-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 8,9-diethyl-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 8,9-diethyl-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 10-chloro-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 10-chloro-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-chloro-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-chloro-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 8-chloro-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 8-chloro-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-bromo-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-amino-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-amino-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-acetylamino-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-propylsulfonyl-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-ethylsulfinyl-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-hydroxy-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 8-hydroxy-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 2-hydroxymethyl-9-methoxy-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-methoxy-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-ethoxy-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-pentyloxy-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-ethylthio-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-ethylthio-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; 9-ethylamino-2-hydroxymethyl-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives; and 9-ethylamino-2-(tetrazol-5-yl)-1,2,4-triazolo[1,5-c]quinazolin-5-one and its 6-methyl, 6-ethyl, 6-propyl, 6-isopropyl, 6-cyclopropyl, 6-n-butyl, 6-sec.-butyl, 6-tert.-butyl, 6-allyl, 6-buten-2-yl, 6-buten-3-yl, 6-n-pentyl, 6-pentenyl, 6-isoamyl, 6-hexyl, 6-hexenyl, 6-benzyl, 6-heptyl, 6-methoxyethyl, 6-methoxyethoxymethyl and 6-ethoxyethoxymethyl derivatives.

The novel compounds and their physiologically tolerated salts are useful drugs in the treatment of allergic disorders of the respiratory tract, the gastrointestinal tract and the skin, for example the treatment of allergic asthma, allergic rhinitis or food allergies.

The anti-allergic action was tested on rats, using the passive cutaneous anaphylaxis (PCA) model.

Narcotized male rats (100 to 140 g) are sensitized by intradermal injection (into the shaved dorsal skin) of 0.1 ml of an ovalbumin antiserum. After a sensitization period of about 48 hours, the treatment (intraperitoneal or oral administration) is carried out with various dosages (10 animals/dose) of the test substances. 15–20 minutes after treatment, an antigen/Evans blue mixture (10 mg/kg of ovalbumin in 2% strength Evans blue solution) is injected intravenously into the test animals. 30 minutes later, the animals are sacrificed, the dorsal skin is removed and the diameter of the circular blue coloration is measured on the inner surface. The size of the color patches of untreated control animals can be standardized. Anti-allergic substances reduce the diameter of the color patch by an amount dependent on the dose. The ED 50% is quoted as the dose which reduces the diameter of the color patch by 50% relative to that of non-medicated control animals. In addition to the anti-allergic action, the acute toxicity was determined for intraperitoneal administration, using groups of 2 NMRI mice, each weighing 20–26 g, and for oral administration, using groups of 2 Sprague-Dawley rats, each weighing 120–150 g. The LD 50 was determined on groups of 10 NMRI mice, each weighing 20–26 g, after intraperitoneal administration. The post-observation period was 14 days.

The compounds according to the invention are highly active as anti-allergics. Table 1 shows that these compounds are from 4.4 (Example 17) to 1.2 (Example 27) times more active than the comparative compound Pirquinozol (J. Pharmacol. Exp. Ther., 213 (1980) 432–436, and JAMA, 242 (1979), 1912. In this test method, the reference substance Cromolyne is inactive in oral doses of up to 100 mg/kg.

As regards the acute toxicity, the novel compounds differ slightly or insignificantly from the comparative compounds. However, because of the greater activity, the quotient of the toxic dose to the effective dose is greater.

TABLE 1

Anti-allergic action of the oral administration.
PCA. Rats

| Example | Inhibition of PCA in rats ED 50% mg/kg | R.A. |
|---|---|---|
| 13 | 0.518 | 2.29 |
| 14 | 0.707 | 1.68 |
| 17 | 0.271 | 4.39 |
| 25 | 0.617 | 1.92 |
| 20 | 0.723 | 1.64 |
| 28 | 0.876 | 1.36 |
| 27 | 1.00 | 1.19 |
| Pirquinozol | 1.19 | 1.00 |
| Cromolyne | >100 | — |

R.A.: relative activity, Pirquinozol = 1.00

On the basis of the results shown in Table 1, a particularly preferred meaning of X is carboethoxy, particularly preferred meanings for $R^1$ and $R^2$ are hydrogen, chlorine and methyl, and particularly preferred meanings of $R^3$ are methyl and ethyl.

For therapeutic use, individual doses of 0.1–100 mg are employed.

Accordingly, the present invention also relates to therapeutic agents or formulations which, in addition to conventional pharmaceutical carriers, diluents and auxiliaries, contain a compound of the formula I as the active compound, and to the use of the novel compounds in the treatment of allergic disorders.

The preferred formulations are those suitable for oral administration. They include, for example, tablets, film tablets, coated tablets, capsules, pills, powders, solutions, suspensions and depot forms. Inhalation formulations and parenteral formulations, such as injection solutions, may also be used.

The pharmaceutical, solid or liquid, use forms are prepared in a conventional manner. To do so, the active compounds can be compounded with the conventional pharmaceutical auxiliaries, such as talc, gum arabic, sucrose, lactose, grain starch or corn starch, potato flour, magnesium stearate, alginates, gum tragacanth, carraghenates, polyvinyl alcohol, polyvinylpyrrolidone, aqueous or non-aqueous carriers, wetting agents, dispersants, emulsifiers and/or preservatives (cf. R. Voigt, Lehrbuch der pharmazeutischen Technologie, VEB Verlag Volk und Gesundheit, Berlin 1977).

Preparation of the starting compounds:

EXAMPLE I 2-chloro-4-hydrazinoquinazoline 87 g (1.74 moles) of hydrazine hydrate were added dropwise to a suspension of 86.5 g (0.43 mole) of 2,4-dichloroquinazoline in 1500 ml of methylene chloride at room temperature, while cooling with ice and stirring vigorously. After 8 hours at room temperature, the precipitate was filtered off under suction, washed with water and dried. Yield: 78.4 g (92%) of 2-chloro-4-hydrazinoquinazoline, mp.>280° C.

The compounds below were prepared by the same process (the melting points are above the measuring limit of 280° C. of the melting point apparatus):

4-hydrazino-2,6,8-trichloroquinazoline, mp.>280° C., yield 66%

2-chloro-4-hydrazino-6-methylquinazoline, mp.>280° C., yield 73%

2,6-dichloro-4-hydrazinoquinazoline, mp.>280° C. yield 80%

2-chloro-5-fluoro-4-hydrazinoquinazoline, mp.>280° C., yield 79%

2-chloro-4-hydrazino-6,7-methylenedioxyquinazoline, mp.>280° C., yield 84%

EXAMPLE II 2-chloro-4-N-(N'-ethyloxyalylhydrazino)-quinazoline 16.9 g (0.087 mole) of 2-chloro-4-hydrazinoquinazoline were suspended in 400 ml of absolute methylene chloride/14 ml of triethylamine, and 14.2 g (0.104 mole) of ethoxyoxalyl chloride were added, while cooling with ice. The mixture was stirred overnight at room temperature, and the precipitate was filtered off under suction, washed with water and dried. Yield: 14.6 g (57%), mp. 211° C.

$C_{12}H_{11}N_4O_3Cl$ (295): Calculated: 48.9 C; 3.8 H; 19.0 N; 12.0 Cl; Found: 48.9 C; 4.0 H; 19.3 N; 12.2 Cl.

The compounds below were prepared from the corresponding starting compounds and oxalates, using a similar procedure:

4-N-(N'-ethyloxalylhydrazino)-2,6,8-trichloroquinazoline, mp. 154°-158° C., Yield 52%

2,6-dichloro-4-N-(N'-ethyloxalylhydrazino)-quinazoline, yield 56%

2-chloro-4-N-(N'-ethyloxalylhydrazino)-5-fluoroquinazoline, yield 56%

2-chloro-4-N-(N'-ethyloxalylhydrazino)-6-methylquinazoline, yield 59%

2-chloro-4-N-(N'-ethyloxalylhydrazino)-6,7-methylenedioxyquinazoline, yield 88%

2-chloro-4-N-(N'-isoamyloxalylhydrazino)-quinazoline, mp. 209°-211° C., yield 38%

2-chloro-4-N-(N'-cyclohexyloxalylhydrazino)-quinazoline, mp. 220°-221° C., yield 40%

4-N-(N'-benzyloxalylhydrazino)-2-chloroquinazoline, mp. 217°-218° C., yield 66%

Preparation of the compounds according to the invention:

EXAMPLE 1

Ethyl 1,2,4-triazolo[1,5-c]quinazolin-5-one-2-carboxylate 57 g (0.19 mole) of 2-chloro-4-N-(N'-ethyloxalylhydrazino)-quinazoline in 900 ml of acetic acid were refluxed for 4 hours, the solvent was distilled off, and the residue was stirred with water and dried. Yield: 36 g (73%), mp.: 279° C.

$C_{12}H_{10}N_4O_3$ (258): Calculated: 55.8 C; 3.9 H; 21.7 N; Found: 55.9 C; 4.3 H; 21.8 N.

Each of the compounds below was prepared from the chloro compound in the same manner:

EXAMPLE 2

Ethyl 9-methyl-1,2,4-triazolo[1,5-c]quinazolin-5-one-2-carboxylate

Mp.: 286°-287° C., yield: 72%.

$C_{13}H_{12}N_4O_3$ (272); Calculated: 57.4 C; 4.4 H; 20.6 N; Found: 57.0 C; 4.4 H; 20.3 N.

EXAMPLE 3

Ethyl 7,9-dichloro-1,2,4-triazolo[1,5-c]quinazolin-5-one-2-carboxylate

Mp.: 265°-269° C., yield: 48%.

$C_{12}H_8Cl_2N_4O_3$ (327): Calculated: 44.0 C; 2.4 H; 17.1 N; 21.7 Cl; Found: 43.8 C; 2.6 H; 17.5 N; 21.2 Cl.

EXAMPLE 4

Ethyl 9-chloro-1,2,4-triazolo[1,5-c]quinazolin-5-one-2-carboxylate

Mp.: 280° C., yield: 60%.

$C_{12}H_9ClN_4O_3$ (292): Calculated: 49.3 C; 3.1 H; 19.1 N; 12.1 Cl; Found: 49.3 C; 3.2 H; 19.5 N; 12.2 Cl.

EXAMPLE 5

Ethyl 10-fluoro-1,2,4-triazolo[1,5-c]quinazolin-5-one-2-carboxylate

Mp.: 290°-291° C., yield: 31%.

$C_{12}H_9FN_4O_3$ (276): Calculated: 52.2 C; 3.3 H; 20.3 N; 6.9 F; Found: 52.1 C; 3.3 H; 20.0 N; 6.8 F.

EXAMPLE 6

Ethyl 8,9-methylenedioxy-1,2,4-triazolo[1,5-c]quinazolin-5-one-2-carboxylate

Mp.: 281° C., yield: 72%.

$C_{13}H_{10}N_4O_5 \cdot 0.5 H_2O$ (311): Calculated: 50.2 C; 3.5 H; 18.0 N. Found: 50.2 C; 3.7 H; 17.6 N.

EXAMPLE 7

Isoamyl 1,2,4-triazolo[1,5-c]quinazolin-5-one-2-carboxylate

Mp.: 215°-219° C., yield: 61%.

$C_{15}H_{16}N_4O_3$ (300): Calculated: 60.0 C; 5.4 H; 18.7 N; Found: 59.9 C; 5.4 H; 18.8 N.

EXAMPLE 8

Cyclohexyl 1,2,4-triazolo[1,5-c]quinazolin-5-one-2-carboxylate

Mp.: 255°-257° C., yield: 81%.

$C_{16}H_{16}N_4O_3$ (312): Calculated: 61.5 C; 5.2 H; 17.9 N; Found: 61.6 C; 5.2 H; 17.9 N.

EXAMPLE 9

Ethyl 8,9-dimethoxy-1,2,4-triazolo[1,5-c]quinazolin-5-one-2-carboxylate

Mp.: 290° C., yield: 28%.

$C_{14}H_{14}N_4O_5$ (318): Calculated: 52.8 C; 4.4 H; 17.6 N; Found: 52.4 C; 4.5 H; 17.4 N.

EXAMPLE 10

Ethyl 8-trifluoromethyl-1,2,4-triazolo[1,5-c]quinazolin-5-one-2-carboxylate

Mp.: 290° C., yield: 33%.

$C_{13}H_9F_3N_4O_3$ (326): Calculated: 47.9 C; 2.8 H; 17.2 N; 17.5 F; Found: 47.7 C; 2.8 H; 17.3 N; 17.4 F.

EXAMPLE 11

Ethyl 9-N,N-dimethylaminosulfonyl-1,2,4-triazolo[1,5-c]quinazolin-5-one-2-carboxylate Mp.: 288°–290° C., yield: 38%.

$C_{14}H_{15}N_5O_5S$ (365): Calculated: 46.0 C; 4.1 H; 19.2 N; Found: 46.3 C; 4.5 H; 19.0 N.

EXAMPLE 12

Ethyl 9-methylthio-1,2,4-triazolo[1,5-c]quinazolin-5-one-2-carboxylate

Mp.: 277°–278° C., yield: 31%.

$C_{13}H_{12}N_4O_3S$ (304): Calculated: 51.3 C; 4.0 H; 18.4 N; Found: 51.6 C; 4.2 H; 18.1 N.

EXAMPLE 13

Ethyl 6-methyl-1,2,4-triazolo[1,5-c]quinazolin-5-one-2-carboxylate 12.0 g (0.047 mole) of ethyl 1,2,4-triazolo[1,5-c]quinazolin-5-one-2-carboxylate in 100 ml of absolute dimethylformamide were added dropwise to a suspension of 0.053 mole of NaH in 100 ml of absolute dimethylformamide at room temperature. After 2 hours, 7.5 g (0.053 mole) of methyl iodide were added, and the mixture was stirred overnight at room temperature and then poured into 400 ml of ice water. The precipitate was filtered off under suction and dried. Yield: 6.6 g (52%), mp.: 258° C.

$C_{13}H_{12}N_4O_3$ (272): Calculated: 57.4 C; 4.4 H; 20.6 N; Found: 57.5 C; 4.8 H; 20.6 N.

The compounds below, inter alia, were prepared by the above method, the appropriate alkyl iodide, benzyl bromide, allyl bromide or methoxyethoxymethyl chloride being used as a reactant.

EXAMPLE 14

Ethyl 6-ethyl-1,2,4-triazolo[1,5-c]quinazolin-5-one-2-carboxylate

Mp.: 207°–209° C., yield: 38%.

$C_{14}H_{14}N_4O_3$ (286): Calculated: 58.7 C; 4.9 H; 19.6 N; Found: 58.5 C; 4.9 H; 19.8 N.

EXAMPLE 15

Ethyl 6-propyl-1,2,4-triazolo[1,5-c]quinazolin-5-one-2-carboxylate

Mp.: 203°–204° C., yield: 42%.

$C_{15}H_{16}N_4O_3$ (300): Calculated: 60.0 C; 5.4 H; 18.7 N; Found: 59.6 C; 5.3 H; 18.8 N.

EXAMPLE 16

Ethyl 6-heptyl-1,2,4-triazolo[1,5-c]quinazolin-5-one-2-carboxylate

Mp.: 203°–204° C., yield: 42%.

$C_{19}H_{24}N_4O_3$ (356): Calculated: 64.0 C; 6.8 H; 15.7 N; Found: 64.2 C; 7.2 H; 15.5 N.

EXAMPLE 17

Ethyl 6-ethyl-9-methyl-1,2,4-triazolo[1,5-c]quinazolin-5-one-2-carboxylate

Mp.: 175°–178° C., yield: 43%.

$C_{15}H_{16}N_4O_3$ (300): Calculated: 60.0 C; 5.4 H; 18.7 N; Found: 59.6 C; 5.4 H; 18.4 N.

EXAMPLE 18

Ethyl 6-benzyl-1,2,4-triazolo[1,5-c]quinazolin-5-one-2-carboxylate

Mp.: 207°–211° C., yield: 90%.

$C_{19}H_{16}N_4O_3$ (348): Calculated: 65.5 C; 4.6 H; 16.1 N; Found: 66.0 C; 4.9 H; 15.8 N.

EXAMPLE 19

Ethyl 6-allyl-1,2,4-triazolo[1,5-c]quinazolin-5-one-2-carboxylate

Mp.: 168°–172° C., yield: 35%.

$C_{15}H_{14}N_4O_3$ (298): Calculated: 60.4 C; 4.7 H; 18.8 N; Found: 60.3 C; 4.7 H; 19.2 N.

EXAMPLE 20

Ethyl 9-chloro-6-methyl-1,2,4-triazolo[1,5-c]quinazolin-5-one-2-carboxylate

Mp.: 250°–254° C., yield: 92%.

$C_{13}H_{11}ClN_4O_3$ (306): Calculated: 50.9 C; 3.6 H; 18.3 N; 11.6 Cl; Found: 51.0 C; 4.1 H; 17.9 N; 11.3 Cl.

EXAMPLE 21

Ethyl 10-fluoro-6-methyl-1,2,4-triazolo[1,5-c]quinazolin-5-one-2-carboxylate

Mp.: 290° C., yield: 61%.

$C_{13}H_{11}FN_4O_3$ 290: Calculated: 53.8 C; 3.8 H; 19.3 N; 6.6 F; Found: 53.4 C; 3.8 H; 19.1 N; 6.4 F.

EXAMPLE 22

Ethyl 8,9-methylenedioxy-6-methyl-1,2,4-triazolo[1,5-c]quinazolin-5-one-2-carboxylate Mp.: 290° C., yield: 42%.

$C_{14}H_{12}N_4O_5$ (316): Calculated: 53.2 C; 3.8 H; 17.7 N; Found: 53.0 C; 3.9 H; 17.8 N.

EXAMPLE 23

Ethyl 6-ethyl-8,9-methylenedioxy-1,2,4-triazolo[1,5-c]quinazolin-5-one-2-carboxylate Mp.: 281°–286° C., yield: 56%.
$C_{15}H_{14}N_4O_5$ (330): Calculated: 54.6 C; 4.3 H; 17.0 N; Found: 54.2 C; 4.4 H; 16.8 N.

EXAMPLE 24

Ethyl 6-methoxyethoxymethyl-8,9-methylenedioxy-1,2,4-triazolo[1,5-c]quinazolin-5-one-2-carboxylate Mp.: 179°–181° C., yield: 84%.
$C_{17}H_{18}N_4O_7$ (390): Calculated: 52.3 C; 4.6 H; 14.4 N; Found: 51.9 C; 4.6 H; 14.7 N.

EXAMPLE 25

Ethyl 6,9-dimethyl-1,2,4-triazolo[1,5-c]quinazolin-5-one-2-carboxylate

Mp.: 220°–222° C., yield: 49%.
$C_{14}H_{14}N_4O_3$ (286): Calculated: 58.7 C; 4.9 H; 19.6 N; Found: 59.0 C; 5.2 H; 19.2 N.

EXAMPLE 26

Ethyl 8,9-dimethoxy-6-methyl-1,2,4-triazolo[1,5-c]quinazolin-5-one-2-carboxylate Mp.: 290° C., yield: 81%.
$C_{15}H_{16}N_4O_5$ (332): Calculated: 54.2 C; 4.9 H; 16.9 N; Found: 54.2 C; 4.9 H; 17.0 N.

EXAMPLE 27

Ethyl 6,8,9-trimethyl-1,2,4-triazolo[1,5-c]quinazolin-5-one-2-carboxylate

Mp.: 276°–278° C., yield: 94%.
$C_{15}H_{16}N_4O_3$ (300): Calculated: 60.0 C; 5.4 H; 18.7 N; Found: 59.7 C; 5.5 H; 18.5 N.

EXAMPLE 28

Ethyl 8,9-dimethyl-6-ethyl-1,2,4-triazolo[1,5-c]quinazolin-5-one-2-carboxylate

Mp.: 230°–233° C., yield: 58%.
$C_{16}H_{18}N_4O_3$ (314): Calculated: 61.1 C; 5.8 H; 17.8 N; Found: 61.0 C; 5.7 H; 17.8 N.

EXAMPLE 29

Ethyl 8,9-dimethyl-6-propyl-1,2,4-triazolo[1,5-c]quinazolin-5-one-2-carboxylate

Mp.: 218°–221° C., yield: 86%.
$C_{17}H_{20}N_4O_3$ (328): Calculated: 62.2 C; 6.1 H; 17.1 N; Found: 62.5 C; 6.4 H; 16.9 N.

EXAMPLE 30

Ethyl 8,9-dimethyl-6-methoxyethoxymethyl-1,2,4-triazolo[1,5-c]quinazolin-5-one-2-carboxylate Mp.: 154°–157° C., yield: 75%.
$C_{18}H_{22}N_4O_5$ (374): Calculated: 57.8 C; 5.9 H; 15.0 N; Found: 58.0 C; 5.9 H; 14.6 N.

EXAMPLE 31

Ethyl 9-N,N-dimethylaminosulfonyl-6-methyl-B 1,2,4-triazolo[1,5-c]quinazolin-5-one-2-carboxylate Mp.: 290° C., yield: 65%.
$C_{15}H_{17}N_5O_5S$ (379): Calculated: 47.5 C; 4.5 H; 18.5 N; Found: 47.2 C; 4.5 H; 18.4 N.

EXAMPLE 32

Ethyl 6-methyl-8-trifluoromethyl-1,2,4-triazolo[1,5-c]quinazolin-5-one-2-carboxylate Mp.: 221°–224° C., yield: 47%
$C_{14}H_{11}F_3N_4O_3$ (340): Calculated: 49.4 C; 3.3 H; 16.5 N; 16.8 F; Found: 49.7 C; 3.4 H; 16.3 N; 16.5 F.

EXAMPLE 33

Ethyl 6-methyl-9-methylthio-1,2,4-triazolo[1,5-c]quinazolin-5-one-2-carboxylate

Mp.: 239°–240° C., yield: 52%.
$C_{14}H_{14}N_4O_3S \cdot 0.5H_2O$ (327): Calculated: 51.4 C; 4.6 H; 17.1 N; Found: 51.4 C; 4.3 H; 17.1 N.

EXAMPLE 34

Benzyl 6-methyl-1,2,4-triazolo[1,5-c]quinazolin-5-one-2-carboxylate

Mp.: 208°–210° C., yield: 82%.
$C_{18}H_{14}N_4O_3$ (334): Calculated: 64.7 C; 4.2 H; 16.8 N; Found: 64.3 C; 4.9 H; 17.0 N.

EXAMPLE 35

2-Ethoxyethyl 6-ethyl-1,2,4-triazolo[1,5-c]quinazolin-5-one-2-carboxylate 1.4 g (0.005 mole) of ethyl 6-ethyl-1,2,4-triazolo[1,5-c]quinazolin-5-one-2-carboxylate in 15 ml of ethylglycol/0.1 g NaOCH₃ were stirred for 90 minutes at 120° C., the solvent was distilled off and the residue was washed with water and dried. Yield: 1.2 g (67%), mp. 137°–141° C.

$C_{16}H_{18}N_4O_4$ (330): Calculated: 58.2 C; 5.5 H; 17.0 N; Found: 58.1 C; 5.4 H; 17.3 N.

EXAMPLE 36

Ethyl 9-nitro-1,2,4-triazolo[1,5-c]quinazolin-5-one-2-carboxylate 2.0 g (0.008 mole) of ethyl 1,2,4-triazolo[1,5-c]quinazolin-5-one-2-carboxylate were introduced into 20 ml of concentrated H₂SO₄ at 20° C., whilst stirring, and 0.3 ml of 100% strength HNO₃ was added dropwise. The mixture was stirred for a further 3 hours at 20° C. and then introduced onto 100 ml of ice water. The precipitate was filtered off and dissolved in methylene chloride/methanol, the solution was treated with active charcoal and filtered, and the solvent was stripped off. Yield: 1.4 g (60%), mp. 280° C.

$C_{12}H_9N_5O_5$ (303): Calculated: 47.5 C; 3.0 H; 23.1 N; Found: 47.3 C; 3.3 H; 22.8 N.

EXAMPLE 37

Preparation of ethyl 6-methyl-9-nitro-1,2,4-triazolo[1,5-c]quinazolin-5-one-2-carboxylate by nitration using the procedure described in Example 36:

Mp.: 157°–165° C., yield: 72%.

$C_{13}H_{11}N_5O_5.0.5H_2O$ (326): Calculated: 47.8 C; 3.7 H; 21.5 N; Found: 47.5 C; 3.6 H; 21.4 N.

EXAMPLE 38

6-Propyl-1,2,4-triazolo[1,5-c]quinazolin-5-one-2-carboxylic acid 1.1 g of $NaHCO_3$ were added to 3.5 g (0.012 mole) of ethyl 6-propyl-1,2,4-triazolo[1,5-c]quinazolin-5-one-2-carboxylate in 50 ml of water, and the mixture was refluxed for 8 hours. It was then filtered, and acidified with dilute HCl, and the precipitate was filtered off under suction and dried. Yield: 1.0 g (32%), mp. 233°–235° C.

$C_{13}H_{12}N_4O_3$ (272): Calculated: 57.4 C; 4.4 H; 20.6 N; Found: 57.0 C; 4.4 H; 20.7 N.

EXAMPLE 39

1,2,4-Triazolo[1,5-c]quinazolin-5-one-2-carboxylic acid 5 g (15.6 mmoles) of benzyl 1,2,4-triazolo[1,5-c]quinazolin-5-one-2-carboxylate were dissolved in 250 ml of methanol, 1 g of 5% strength Pd/C was added, and the mixture was then stirred under atmospheric pressure in a hydrogenation apparatus until the absorption of hydrogen was complete. The precipitate was filtered off under suction and dissolved in 50 ml of hot dimethylformamide, the solution was filtered and the solvent was distilled off. The residue was digested with methanol and dried.

Yield: 1.3 g (36%), mp.: 290° C.

$C_{10}H_6N_4O_3$ (230): Calculated: 52.2 C; 2.6 H; 24.3 N; Found: 52.0 C; 2.9 H; 24.2 N.

EXAMPLE 40

Preparation of 6-methyl-1,2,4-triazolo[1,5-c]quinazolin-5-one-2-carboxylic acid by hydrogenolysis using the procedure described in Example 39:

Mp.: 290° C., yield: 34%.

$C_{11}H_8N_4O_3.H_2O$ (262): Calculated: 50.4 C; 3.8 H; 21.4 N; Found: 50.6 C; 4.0 H; 21.3 N.

EXAMPLE 41

6-Methyl-1,2,4-triazolo[1,5-c]quinazolin-5-one-2-carboxamide 12.0 g of ethyl 6-methyl-1,2,4-triazolo[1,5-c]quinazolin-5-one-2-carboxylate were suspended in 600 ml of absolute dimethylformamide, and 200 ml of a 7% strength methanolic $NH_3$ solution were added. The mixture was stirred for 48 hours, after which the precipitate was filtered off under suction, washed with dimethylformamide and water, and dried. Yield: 4.8 g (42%), mp. 286°–287° C.

$C_{11}H_9N_5O_2$ (243): Calculated: 54.3 C; 3.7 H; 28.8 N; Found: 54.2 C; 3.9 H; 28.1 N.

EXAMPLE 42

6-Methyl-1,2,4-triazolo[1,5-c]quinazolin-5-one-2-carboxylic acid nitrile 20 g (0.082 mole) of 6-methyl-1,2,4-triazolo[1,5-c]quinazolin-5-one-2-carboxamide in 600 ml of $POCl_3$ were refluxed for 3 hours, the solvent was stripped off, the residue obtained was poured onto ice and the precipitate was filtered off under suction. Yield: 17.4 g (94%), mp,: 270° C., IR (KI): 2,260 $cm^{-1}$ (CN).

EXAMPLE 43

6-Methyl-2-(tetrazol-5-yl)-1,2,4-triazolo[1,5-c]quinazolin-5-one.tris-(hydroxymethyl)-aminomethane 5 g (22.2 mmoles) of the nitrile from Example 42 were stirred with 16 g of $NaN_3$ and 1.3 g of $NH_4Cl$ in 100 ml of absolute dimethylformamide for 3 hours at 90° C. After the mixture had cooled, it was poured onto 400 ml of ice water and filtered, and the filtrate was acidified. The precipitated solid (2.4 g) was stirred with 0.86 g of tris-(hydroxymethyl)-aminomethane in 10 ml of water, and the solution was filtered and evaporated down. The residue was treated with methanol and dried. Yield: 1.8 g (21%), mp.: 266°–268° C.

$C_{15}H_{19}N_9O_4$ (389): Calculated: 46.3 C; 4.9 H; 32.3 N; Found: 46.3 C; 4,8 H; 32.0 N.

EXAMPLE 44

Ethyl 6-methyl-9-methylsulfonyl-1,2,4-triazolo[1,5-c]quinazolin-5-one-2-carboxylate 0.5 g (1.57 mmoles) of ethyl 6-methyl-9-methylthio-1,2,4-triazolo[1,5-c]quinazolin-5-one-2-carboxylate was suspended in 25 ml of $CH_2Cl_2$/0.5 ml of $CH_3OH$, a solution of 0.3 g (1.57 mmoles) of m-chloroperbenzoic acid in $CH_2Cl_2$ was added at room temperature, and the mixture was stirred overnight. It was then filtered, the filtrate was washed with aqueous $NaHCO_3$ solution and the solvent was stripped off. After treatment with ether, the residue gave 0.3 g (53%) of product of melting point 277°–279° C.

EXAMPLES OF PHARMACEUTICAL FORMULATIONS

| Tablets | | |
|---|---|---|
| (a) Active compound | | 0.100 g |
| Stearic acid | | 0.010 g |
| Glucose | | 1.890 g |
| | | 2.000 g |
| (b) Active compound | | 0.020 g |
| Stearic acid | | 0.020 g |
| Glucose | | 1.960 g |
| | | 2.000 g |

The constituents are converted to tablets, having the above composition, in a conventional manner.

| Inhalation aerosol | |
|---|---|
| Active compound | 1.00 part |
| Soya bean lecithin | 0.20 part |
| Propellant gas mixture (Frigen 11, 12 and 114) to make up to | 100.00 parts |

The formulation is preferably packaged in aerosol containers having a dosing valve, and so arranged that a single operation dispenses a dose of 5–20 mg of active compound.

| Ampoules (injection solutions) | |
|---|---|
| Active compound | 50.0 parts by weight |
| Sodium pyrosulfite | 1.0 part by weight |
| Disodium ethylenediaminetetra- | 0.5 part by weight |

| Ampoules (injection solutions) | |
|---|---|
| acetate | |
| Sodium chloride | 8.5 parts by weight |
| Doubly distilled water to make up to | 1,000.0 parts by weight |

The active compound and the auxiliaries are dissolved in a sufficient amount of water and brought to the desired concentration with the required amount of water. The solution is filtered, and introduced into 1 ml ampoules under aseptic conditions. Finally, the ampoules are sterilized and sealed. Each ampoule contains 50 mg of active compound.

We claim:

1. A compound of the formula I

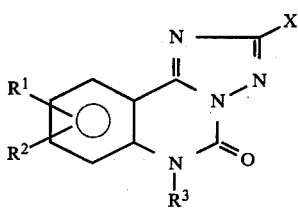

where X is carboxyl which may be in the form of a salt with a physiologically tolerated amine or metal cation, or is

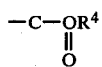

where $R^4$ is alkyl of 1 to 8 carbon atoms, cycloalkyl of 3 to 8 ring carbon atoms, benzyl, or —(CH$_2$)$_n$—O—R$^5$ or

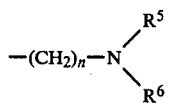

where n is an integer from 2 to 4 and $R^5$ and $R^6$ are each alkyl of 1 to 3 carbon atoms, or X is hydroxymethyl, nitrile, tetrazolyl, carbonylaminotetrazolyl or carbamyl, and $R^1$ and $R^2$ are identical or different and are each hydrogen, fluorine, chlorine, bromine, alkyl of 1 to 5 carbon atoms, trifluoromethyl, nitro, amino, an alkyl, monoalkylamino or dialkylamino group where alkyl is of 1 to 5 carbon atoms, alkoxy where alkyl is of 1 to 6 carbon atoms, or an alkylthio, alkylsulfenyl, alkylsulfonyl or dialkylaminosulfonyl radical where alkyl is of 1 to 6 carbon atoms, or $R^1$ and $R^2$ together form an alkylenedioxy group —O—(CH$_2$)$_n$—O— where n is 1 or 2, or an alkylene group —(CH$_2$)$_n$— where n is 3, 4 or 5, and $R^3$ is hydrogen, alkyl which is of 1 to 7 carbon atoms and may or may not be interrupted by 1 or 2 oxygen atoms, alkenyl of 2 to 7 carbon atoms or aralkyl of 7 to 10 carbon atoms, and its physiologically tolerated salts with acids.

2. A compound of the formula I as claimed in claim 1, wherein X is

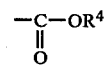

where $R^4$ is alkyl of 1 to 4 carbon atoms, $R^1$ and $R^2$, which may be identical or different, are each hydrogen, fluorine, chlorine, bromine or alkyl of 1 to 3 carbon atoms and $R^3$ is alkyl of 1 to 4 carbon atoms.

3. A compound of the formula I as claimed in claim 1, wherein X is carboethoxy, $R^1$ and $R^2$ are each hydrogen, chlorine or methyl and $R^3$ is methyl or ethyl.

4. Ethyl 6-ethyl-9-methyl-1,2,4-triazolo[1,5-c]quinazolin-5-one-2-carboxylate and its physiologically tolerated addition salts with acids.

5. Ethyl 6-methyl-1,2,4-triazolo[1,5-c]quinazolin-5-one-2-carboxylate and its physiologically tolerated addition salts with acids.

6. A therapeutic composition for treating allergic disorders which comprises: a pharmaceutically acceptable carrier and an effective amount of a compound of the formula I of claim 1 as the active agent.

7. A therapeutic composition for treating allergic disorders which comprises: a pharmaceutically acceptable carrier and an effective amount of the compound of claim 4 as the active agent.

8. A therapeutic composition for treating allergic disorders which comprises: a pharmaceutically acceptable carrier and an effective amount of the compound of claim 5 as the active agent.

9. A process for treating allergic disorders which comprises: administering orally, parenterally or by inhalation a composition as set forth in claim 6 in individual doses containing from 0.1 to 100 mg of active agent.

10. A process for treating allergic disorders which comprises: administering orally, parenterally or by inhalation the composition set forth in claim 7 in individual doses containing from 0.1 to 100 mg of active agent.

11. A process for treating allergic disorders which comprises: administering orally, parenterally or by inhalation the composition set forth in claim 8 in individual doses containing 0.1 to 100 mg of active agent.

* * * * *